(12) United States Patent
Fidoe et al.

(10) Patent No.: US 6,482,483 B1
(45) Date of Patent: Nov. 19, 2002

(54) PHOSPHONIUM SALT COMPOSITION

(75) Inventors: Stephen David Fidoe, Worcestershire (GB); Christopher David Imrie, Staffordshire (GB); Christopher Raymond Jones, Nr. Walsall (GB); Robert Eric Talbot, Staffordshire (GB)

(73) Assignee: Rhodia Consumer Specialties Limited, West Midlands (GB)

( * ) Notice: Subject to any disclaimer, the term of this patent is extended or adjusted under 35 U.S.C. 154(b) by 0 days.

(21) Appl. No.: 09/509,874

(22) PCT Filed: Oct. 2, 1998

(86) PCT No.: PCT/EP98/06290

§ 371 (c)(1), (2), (4) Date: Apr. 3, 2000

(87) PCT Pub. No.: WO99/17614

PCT Pub. Date: Apr. 15, 1999

(30) Foreign Application Priority Data

Oct. 4, 1997 (GB) .............................................. 9721021

(51) Int. Cl.$^7$ .............................. C07F 9/34; C07F 9/36; C07F 9/42; C07F 9/44; C14C 3/08
(52) U.S. Cl. .................. 428/35.7; 252/8.57; 252/182.3; 252/389.23; 252/400.2; 252/400.23; 252/601; 424/601; 428/339; 428/403; 428/407
(58) Field of Search ................................ 428/35.7, 339, 428/403, 407, 921; 252/8.57, 182.3, 389.23, 400.2, 400.23, 601; 424/601

(56) References Cited

U.S. PATENT DOCUMENTS 4,552,591 A * 11/1985 Millar ...................... 106/18.33
4,692,494 A * 9/1987 Sonenstein .................... 525/57
5,741,757 A * 4/1998 Cooper et al. .............. 504/153

OTHER PUBLICATIONS

Database WPI, Section CH, Week 9602, Derwent Publications Ltd., London, GB: Class A60, AN 96–107334 XP002092999 of JP 07 292152 A (Fujimasu J) Nov. 7, 1995—English Abstract Supplied.

* cited by examiner

Primary Examiner—Sandra M. Nolan
(74) Attorney, Agent, or Firm—Frishauf, Holtz, Goodman & Chick, P.C.

(57) ABSTRACT

A composition comprising tris(hydroxymethyl)phosphine or phosphorus-containing salts or condensates of those salts with nitrogen-containing compounds coated or absorbed onto a solid or porous substrate is disclosed. The salts or condensates are based on tetrakis(hydroxymethyl) phosphonium salts. The substrate has a melting point greater than 70° C. and is an optionally hydroxyl-substituted di- or polycarboxylic acid. The compositions may be used with water soluble film forming polymers to make sachets or bags containing sachets or bags of these phosphorous-containing compositions along with sachets or bags of compositions that are incompatible with these phosphorous-containing compositions.

4 Claims, No Drawings

PHOSPHONIUM SALT COMPOSITION

The present invention relates to a solid composition comprising trishydroxymethl phosphine or a tetrakis (hydroxymethyl) phosphonium salt, collectively referred to herein as "THP".

THP and in particular the salts, notably the chloride (THPC) sulphate (THPS) and phosphate (THPP) have been used for more than forty years as fire retardants. More recently THP salts, and particularly THPS, have found applications as biocides in water treatment in a variety of systems including cooling water, chemical process water and oilfields (see for example EP 0 139 404, EP 0 215 562 and EP 0 293 152), in agriculture, horticulture and medicine (see EP 0 223 533, EP 0 275 207 and EP 0 293 152) and for the treatment of skins during tanning (e.g. EP 0 559 867 and EP 0 681 030).

THP is only available commercially as an aqueous solution. Despite its having been in commercial use for many years, all attempts to prepare THP as a stable solid, e.g. by recrystalising from glacial acetic acid and vacuum drying, have proved unsuccessful due to the highly hygroscopic and unstable nature of the solid product. Lack of a stable solid form of THP has severely restricted, or prevented, it's use in certain applications.

We have now discovered that by coating a solid particulate acid, which is not chemically reactive with THP, with THP at temperatures, preferably, below 60° C. we can obtain a stable, particulate solid THP. We have further discovered that the resulting powder can be compacted to form, e.g., tablets.

The invention provides a composition comprising a particulate or porous, THP-compatible, solid, acid substrate having coated thereon or absorbed therein THP.

The invention further provides a tablet, granule or pellet formed by compacting a particulate composition as aforesaid.

According to a third aspect the invention provides a method of preparing a solid THP composition which comprises coating a solid, particulate, THP-compatible acid with a solution of THP at a temperature between 30 and 60° C.

The solid acid preferably has a melting point above 50° C., more preferably above 60° C., e.g. above 70° C. It is preferably an organic acid, especially a di-, poly-, unsaturated, aromatic or hydroxy-carboxylic acid and particularly one having up to 10 carbon atoms such as oxalic, malonic, succinic, glutaric, adipic, pimelic, suberic, azelaic, citric, tartaric, maleic, fumaric, crotonic, itaconic, aconitic, citraconic, phthalic, benzoic, lactic, angelic or tiglic acids. Higher melting fatty acids such as oleic or stearic may also be used.

The particle size of the substrate is preferably fine, e.g. between 1 micron and 1 mm, especially 10 microns to 500 microns, most preferably 50 microns to 100 microns.

The composition of the invention may conventionally be prepared by fluidising the particulate substrate and spraying an aqueous solution of the THP, preferably a concentrated solution, into the bed. The solution preferably contains more than 20%, especially more than 30%, e.g. more than 50%, typically more than 60%, most preferably 70 to 80% THP by weight based on the weight of the solution.

The temperature of spraying should be less than 100° C., especially less than 80° C., preferably less than 70° C., more preferably less than 60° C., e.g. 35 to 50° C., in order to optimise product stability.

An alternative method of making the solid THP is to form a paste of the THP solution with solid substrate, which is extracted and dried.

The THP may be tris(hydroxymethyl phosphine) or any THP salt of a compatible anion, preferably THPS, but optionally THPC or THPP. Alternatively other water soluble THP salts such as bromide, fluoride, phosphite, sulphite, carbonate, acetate, citrate or any other counterion which does not react chemically with the THP ion could be used.

The product preferably contains from 0.1 to 50%, especially 10 to 40%, e.g. 15 to 30% by weight, based on the total weight of the composition, of the THP, and has a moisture content of from 0 to 10%. especially 0.5 to 8%, e.g. 1 to 5%, most preferably 2 to 4% by weight, based on the total weight of the composition.

The powder of our invention may be compacted into tablets using conventional tabletting technology. Particles of water soluble alkaline material such as carbonate maybe incorporated into such tablets to promote the disintegration thereof by effervescent action.

A particularly preferred form of the solid THP-containing composition comprises a water soluble bag made from a water soluble film forming polymer such as polyvinylalcohol (PVA) containing the solid, particulate, granular or pelletised THP. Such bags may contain measured unit doses making controlled dosing simpler, protect the THP against atmospheric deterioration, and prevent contact between the user and the product.

Especially preferred are dual bags in which a sealed water soluble bag of an auxiliary treatment agent is inserted into the bag of solid THP before sealing the latter. Alternatively the bag of THP may be inserted into the bag of auxiliary treatment agent. This permits one-pack dosing of THP with auxiliary treatment agents which are chemically incompatible with THP.

For example, soluble bags containing alkalis such as sodium. ammonium or potassium carbonate or bicarbonate can be incorporated into the bagged formulation (or vice versa) in order to increase the rate of dissolution of the adipic acid. Synergists, surfactants, biopenetrants, corrosion inhibitors, scale inhibitors. ammonium salt to aid dissolution of ferrous sulphide deposits, sequestrants, deflocculants, flocculants, foam inhibitors, antioxidants and other water treatment chemicals, many of which cannot conveniently be stored in aqueous solution with THP because of adverse reactions, can all be combined with solid THP, e.g. by using multiple bags in convenient, single dose bags or sachets.

When THP is intended for us in the leather industry, the multiple bag technique may be used to combine solid THP with a variety of tanning chemicals such as syntans and vegetable or mineral tanning agents.

Examples of tanning agents which may be combined with THP in this way include copolymers of formaldehyde with urea or aryl groups such as phenol, resorcinol or any benzene or naphalene group which has been substituted with one or more hydroxyl, amino, sulphonate, sulphone and/or sulphonamide groups, and polymers and copolymers of unsaturated carboxylic acids such as acrylic, methacrylic, maleic, fumaric, aconitic, itaconic, citraconic, crotonic, isocrotonic, mesaconic, cinammic, angelic and/or tiglic acids optionally including other vinylic monomers such as styrene.

Less preferably, mineral tanning agents such as chrometan, alum, or zirconium or vegetable tannages such as mimosa may be included.

Products of the invention may optionally contain fragrances in amounts sufficient to mask characteristic odours.

THP containing powder, bags and tablets according to the invention may be used in place of liquid THP in any of the known aqueous applications of the latter. They are especially useful in controlling bacterial growth in oilfield drilling muds, in pharmaceutical and veterinary applications and for the treatment of gardens and fishponds to control algae or moss.

EXAMPLE

A 75% wt./wt. solution of THPS in water containing a small amount of a fragrance to mask the characteristic odour of the solution was sprayed as a fine mist onto an air fluidised bed of adipic acid powder at 40° C.

The product was a free flowing powder which contained 17% by weight THPS and 3.2% moisture (both by weight, based on the total weight of the powder). Samples were stored in bottles at ambient temperature, 40° C., −5° C. 0 to 5° C. and samples in watch glasses were exposed to the atmosphere in the laboratory.

After seven weeks no change was observed in any of the samples and there was no evidence of significant moisture gain in the exposed samples. A slight caking of the latter was easily broken up by shaking. The stability of the samples was confirmed by spectroscopic analysis.

EXAMPLE 2

Solid THP −13% w/w THPS on adipic acid was packed into PVA bags, 300 g per pack for single bags, and 300 g solid THPS+150 g sodium bicarbonate for dual bags. The bicarbonate bag was produced first. and sealed prior to being placed into the solid THPS bag.

An industrial cooling tower having a system volume−0.4 $m^3$ was treated. A blank titration was performed on the cooling water prior to addition, then one bag was added to the sump. THPS levels were monitored with time using a field test. kit. A second experiment was performed on a tower, system volume 0.28 $m^3$, where both types of pack were dosed, and the sump monitored for signs of undissolved acid.
Results
0.4 $m^3$ Tower:

|              | THPS Conc./ppm |            |
| ------------ | -------------- | ---------- |
| Time/Minutes | Dual Bag       | Single Bag |
| 20           | 61.2           | 24.5       |
| 40           | 91.8           | 24.5       |
| 60           | 89.8           | 19.4       |
| 80           | 81.6           | 19.4       |
| 120          | 85.7           | 19.4       |
| 150          | 76.5           | 19.4       |
| 180          | 78.2           | 19.6       |

N.B. complete dissolution would give 97.5 ppm.

0.28$m^3$ Tower:

Undissolved adipic acid could be seen in the sump 24 hours after dosing the single bag pack, whereas the dual bag product had completely dissolved in this time.

What is claimed is:

1. A composition comprising a phosphorus containing material coated on or absorbed in a solid or porous acid substrate, wherein said phosphorus-containing material is selected from the group consisting of tris(hydroxymethyl) phosphine (THP), tetrakis(hydroxymethyl) phosphonium salts (THP+ salts) and condensates of said THP+ salts with nitrogen-containing compounds, and wherein said solid or porous acid substrate has a melting point greater than 70° C. and consists essentially of an organic acid selected from the group consisting of:
 (i) saturated di- or poly-carboxylic acids;
 (ii) unsaturated di- or poly-carboxylic acids;
 (iii) aromatic di- or poly-carboxylic acids; and
 (iv) hydroxy-substituted di- or poly carboxylic acids.

2. A composition according to claim 1, wherein said organic acid is adipic acid.

3. A water soluble sachet or bag formed from a water soluble film forming polymer containing a composition comprising a phosphorus containing material coated on or absorbed in a solid or porous acid substrate, wherein said phosphorus-containing material is selected from the group consisting of tris(hydroxymethyl)phosphine (THP), tetrakis(hydroxymethyl)phosphonium salts (THP+ salts) and condensates of said THP+ salts with nitrogen-containing compounds, and wherein said solid or porous acid substrate has a melting point greater than 70° C. and containing at least one other water soluble sachet or bag, a first composition comprising a particulate or porous, solid, acid substrate having coated thereon or absorbed therein a phosphorus-containing material and at least one other composition which is incompatible with said first composition, said first composition and said at least one other composition being separated by including one of said compositions in said other sachet or bag.

4. A water soluble sachet or bag according to claim 3 wherein said at least one other composition comprises an alkali, a water treatment agent and/or a tanning agent.

* * * * *